United States Patent
Markle

(10) Patent No.: US 6,875,622 B1
(45) Date of Patent: Apr. 5, 2005

(54) METHOD AND APPARATUS FOR DETERMINING ELECTROMAGNETIC PROPERTIES OF A PROCESS LAYER USING SCATTEROMETRY MEASUREMENTS

(75) Inventor: Richard J. Markle, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 10/286,012

(22) Filed: Nov. 1, 2002

(51) Int. Cl.[7] .............................................. G01R 31/26
(52) U.S. Cl. ....................................................... 438/14
(58) Field of Search ........................................... 438/14

(56) References Cited

U.S. PATENT DOCUMENTS

| | | | |
|---|---|---|---|
| 6,051,348 A | 4/2000 | Marinaro et al. | 430/30 |
| 6,245,584 B1 | 6/2001 | Marinaro et al. | 438/14 |
| 6,433,878 B1 | 8/2002 | Niu et al. | 356/603 |
| 6,633,831 B2 * | 10/2003 | Nikoonahad et al. | 702/155 |
| 6,673,637 B2 * | 1/2004 | Wack et al. | 438/14 |
| 2002/0135781 A1 | 9/2002 | Singh et al. | 356/601 |

* cited by examiner

*Primary Examiner*—Stacy A. Whitmore
*Assistant Examiner*—Andre' C. Stevenson
(74) *Attorney, Agent, or Firm*—Williams, Morgan & Amerson

(57) ABSTRACT

A method for determining electromagnetic properties of a process layer includes providing a wafer having a grating structure and a process layer formed over the grating structure. The thickness of the process layer is measured. At least a portion of the process layer and the grating structure is illuminated with a light source. Light reflected from the illuminated portion of the grating structure and the process layer is measured to generate a reflection profile. An electromagnetic property of the process layer is determined based on the measured thickness and the reflection profile.

33 Claims, 5 Drawing Sheets

METHOD AND APPARATUS FOR DETERMINING ELECTROMAGNETIC PROPERTIES OF A PROCESS LAYER USING SCATTEROMETRY MEASUREMENTS

BACKGROUND OF THE INVENTION

1. Field of the Invention

This invention relates generally to the field of semiconductor device manufacturing and, more particularly, to a method and apparatus for determining electromagnetic properties of a process layer using scatterometry measurements.

2. Description of the Related Art

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, i.e., local site and worldwide, monitoring. These deficiencies can engender nonoptimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance, whereas an ideal monitoring and diagnostics system for such tools would provide a means of monitoring this variability, as well as providing means for optimizing control of critical parameters.

Semiconductor devices are manufactured from wafers of a substrate material. Layers of materials are added, removed, and/or treated during fabrication to create the electrical circuits that make up the device. The fabrication essentially comprises four basic operations. Although there are only four basic operations, they can be combined in hundreds of different ways, depending upon the particular fabrication process.

The four operations typically used in the manufacture of semiconductor devices are:

- layering, or adding thin layers of various materials to a wafer from which a semiconductor device is produced;
- patterning, or removing selected portions of added layers;
- doping, or placing specific amounts of dopants in the wafer surface through openings in the added layers; and
- heat treatment, or heating and cooling the materials to produce desired effects in the processed wafer.

The various layers used for forming the features have many specialized functions. Certain layers are used to form conductive features, others perform insulating features, and still others are intermediate layers used to enhance the functionality of the processing steps used to pattern and form the functional layers. In some cases, the ability of a layer to perform its intended function is based mostly on its physical properties, such as its material of construction and thickness, while the ability of other layers to perform their intended function rests on electromagnetic properties, such as refractive index, that may vary based on the particular process used to form the layer.

A commonly used conductive layer in a semiconductor device is polysilicon. One important application for a polysilicon layer is in forming a gate electrode in a transistor. To increase the accuracy of the photolithography process used to pattern the polysilicon layer to define the gate electrodes, an anti-reflective coating (ARC) layer, such as silicon oxynitride (SiON), is sometimes formed over the polysilicon layer prior to patterning to minimize notches caused by reflections during photolithographic techniques. A photoresist layer is subsequently formed over the ARC layer and patterned to allow etching of the polysilicon layer. The ARC layer reduces the reflections and allows more effective patterning of the photoresist layer, which ultimately results in more effective formation of the gate electrodes from the polysilicon layer. The ability of an ARC layer to reduce the effects of reflections depends not only on its material of construction (i.e., SiON) and thickness, but also on the refractive index of the layer (i.e., related to reflectivity). The refractive index of the ARC layer may vary depending on the specific processing environment in which it is formed. Because of the variety of factors influencing the effectiveness of an ARC layer, measuring its thickness alone (i.e., during or after the deposition process) is not sufficient to gauge whether it will adequately perform its intended function.

The present invention is directed to overcoming, or at least reducing the effects of, one or more of the problems set forth above.

SUMMARY OF THE INVENTION

One aspect of the present invention is seen in a method for determining electromagnetic properties of a process layer. The method includes providing a wafer having a grating structure and a process layer formed over the grating structure. A thickness of the process layer is measured. At least a portion of the process layer and the grating structure is illuminated with a light source. Light reflected from the illuminated portion of the grating structure and the process layer is measured to generate a reflection profile. An electromagnetic property of the process layer is determined based on the measured thickness and the reflection profile.

BRIEF DESCRIPTION OF THE DRAWINGS

The invention may be understood by reference to the following description taken in conjunction with the accompanying drawings, in which like reference numerals identify like elements, and in which.

Figure 1:
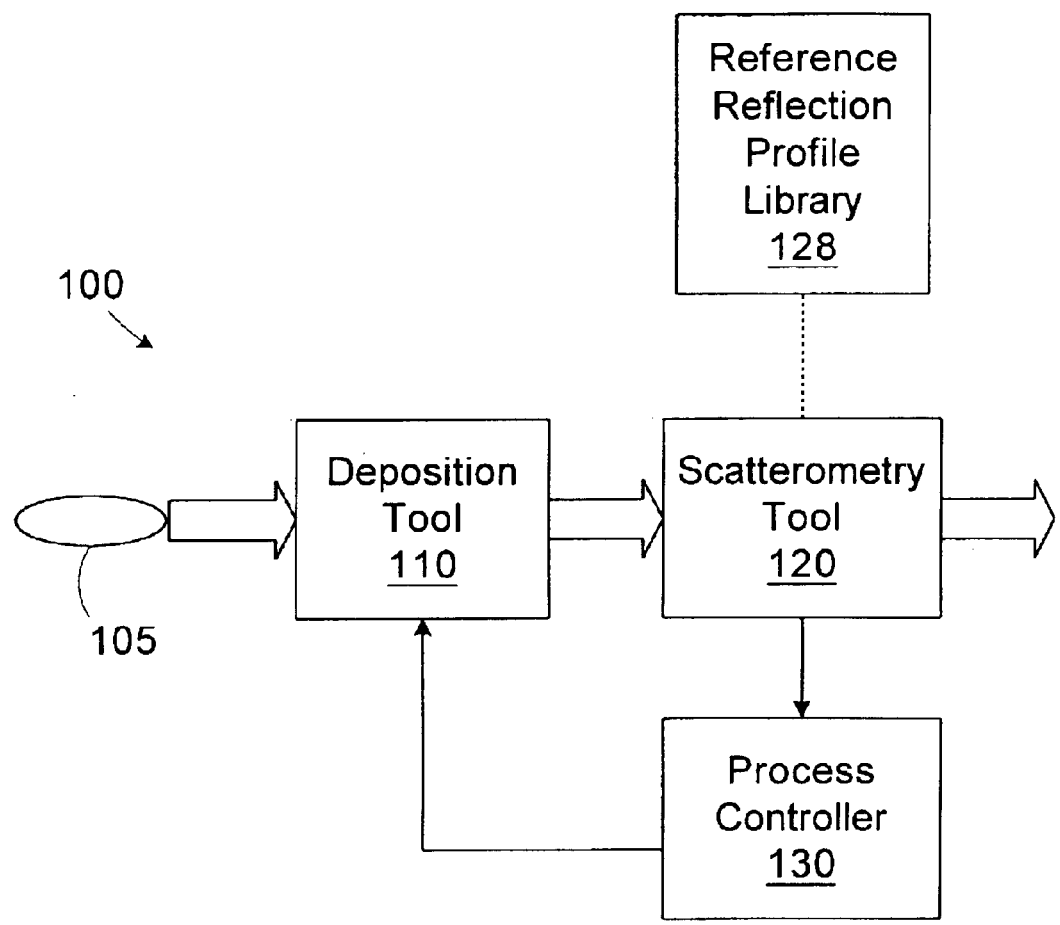
FIG. 1 is a simplified diagram of an illustrative processing line for processing wafers in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Referring to FIG. 1, a simplified diagram of an illustrative processing line 100 for processing wafers 105 in accordance with one illustrative embodiment of the present invention is provided. The processing line 100 includes a deposition tool 110 for depositing a process layer (not shown) on the wafer 105. In the illustrated embodiment, the process layer is one that depends on a particular electromagnetic property to be effective in performing its intended function. For example the process layer may be an antireflective coating (ARC) layer. Variations in the deposition operations of the deposition tool 110 may cause variations in the electromagnetic property of the process layer being deposited.

The processing line 100 includes a scatterometry tool 120 adapted to measure an electromagnetic property of the process layer formed on the wafer 105. In general, the scatterometry tool 120 includes optical hardware, such as an ellipsometer, spectrometer, or reflectometer, and a data processing unit loaded with a scatterometry software application for processing data collected by the optical hardware. For example, the optical hardware may include a model OP5230 or OP5240 with a spectroscopic ellipsometer offered by Thermawave, Inc. of Freemont Calif. The data processing unit may comprise a profile application server manufactured by Timbre Technologies, a fully owned subsidiary of Tokyo Electron America, Inc. of Austin, Tex. and distributed by Thermawave, Inc.

The scatterometry tool 120 may be external to the deposition tool 110 or, alternatively, the scatterometry tool 120 may be installed in an in-situ arrangement. A process controller 130 is provided for controlling the operations of the deposition tool 110 based on the measured electromagnetic property of the deposited process layer. The process controller 130 may provide feedback information to the deposition tool 110 and adjust its operating recipe to control the deposition process for the current wafer being processed or for subsequently processed wafers 105. These feedback and feedforward control techniques will be described in greater detail below.

The reflective index of the process layer typically depends on its thickness, t, its extinction coefficient, k, and its index of refraction, η. To solve for the reflective index using optical measurements, a described below, at least one of the three inputs is fixed. For purposes of this illustration, it is assumed that the thickness of the process layer 310 is measured by the scatterometry tool 120 or a separate thickness metrology tool (not shown) during or after the deposition process. Various thickness metrology tools are known in the art. For example, an Optiprobe tool offered by Therma-Wave, Inc. of Fremont, Calif. may be used to measure the thickness of the process layer 310.

In the illustrated embodiment, the process controller 130 is a computer programmed with software to implement the functions described. However, as will be appreciated by those of ordinary skill in the art, a hardware controller designed to implement the particular functions may also be used. Moreover, the functions performed by the process controller 130, as described herein, may be performed by multiple controller devices distributed throughout a system. Additionally, the process controller 130 may be a stand-alone controller, it may be integrated into a tool, such as the deposition tool 110 or the scatterometry tool 120, or it may be part of a system controlling operations in an integrated circuit manufacturing facility.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the process controller 130, as described, is the Catalyst system offered by KLA-Tencor, Inc. The Catalyst system uses Semiconductor Equipment and Materials International (SEMI) Computer Integrated Manufacturing (CIM) Framework compliant system technologies and is based on the Advanced Process Control (APC) Framework. CIM (SEMI E81-0699 Provisional Specification for CIM Framework Domain Architecture) and APC (SEMI E930999-Provisional Specification for CIM Framework Advanced Process Control Component) specifications are publicly available from SEMI.

In one embodiment, the scatterometry tool 120 measures an electromagnetic property of the process layer as found on features formed in the production devices. For example, the scatterometry tool 120 may measure the reflectivity constant of a process layer deposited over a series of transistor gate electrode stacks or interconnect lines. In some cases, the geometry of the features or the presence of underlying structures may inhibit scatterometry measurements. For example, an ARC layer is not typically deposited directly on a grating structure. Accordingly, a test structure including a grating structure may be employed. The test structures may be formed in a region of the wafer 105 not normally used for forming devices (e.g., in the periphery region where identification codes are typically scribed or in the scribe lines between production die).

Figure 2A:
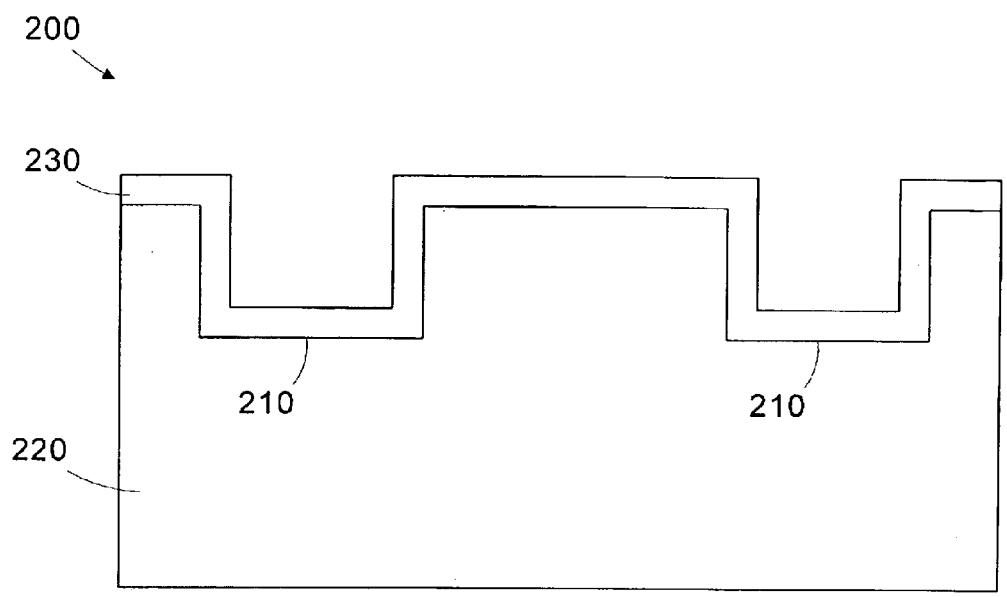
FIGS. 2A and 2B are a cross section views of exemplary semiconductor device test structures.
Figure 2B:
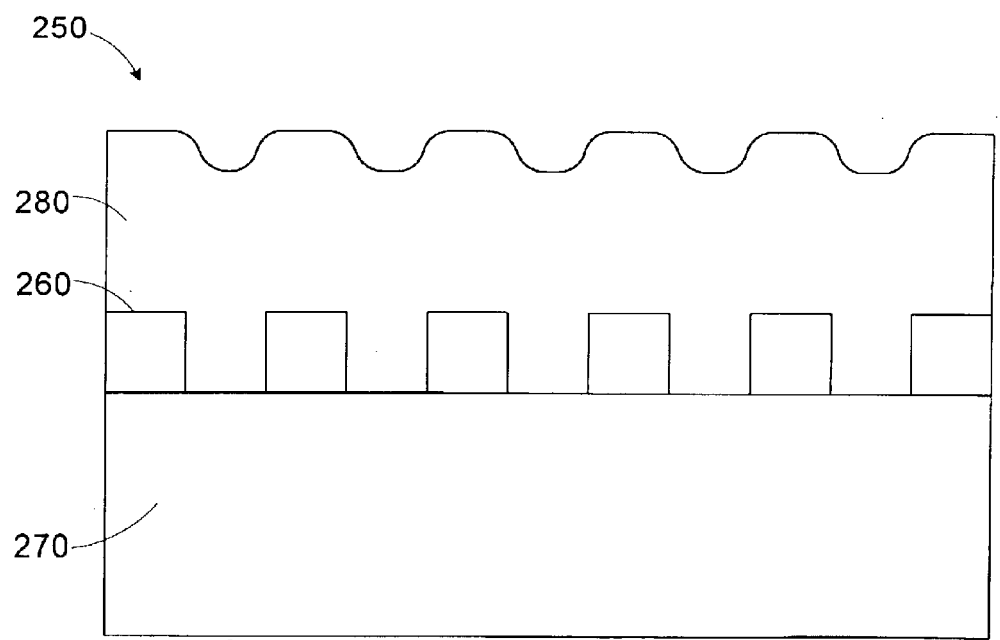

Referring briefly to FIGS. 2A and 2B, exemplary grating structures 200, 250 that may used as test structures on the wafer 105 are shown. The grating structure 200 of FIG. 2A includes trenches 210 formed in a base layer 220. A process layer 230 is formed over the trenches 210. For example, the process layer 230 may be an ARC layer, and the trenches 210 may be formed in a portion of a polysilicon layer in an unused portion of the wafer 105. In FIG. 2B, the grating structure 250 is comprised of a plurality of interconnect structures 260 formed over a base layer 270 and covered by a process layer 280.

Figure 3:
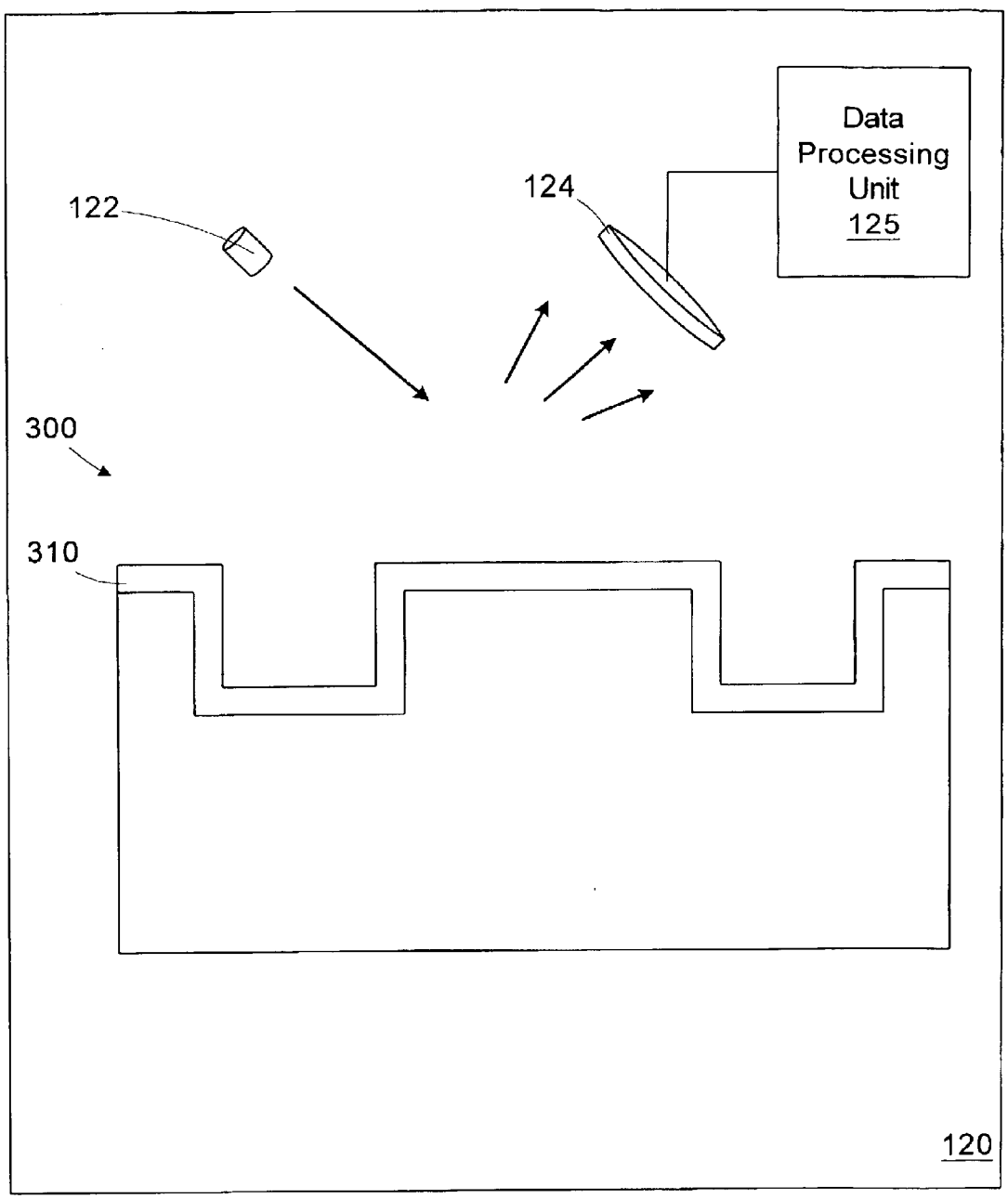
FIG. 3 is a simplified view of the scatterometry tool of FIG. 1 loaded with a wafer including a grating structure.

Turning now to FIG. 3, a simplified view of the scatterometry tool 120 loaded with a wafer 105 having a grating structure 300 and a process layer 310 overlying the grating structure 300 is provided. The grating structure 300 may be comprised of a plurality of features formed in a production device on the wafer 105, or alternatively, the grating structure 300 may be a test structure similar to the grating structures 200, 250 discussed above in reference to FIGS. 2A and 2B. The scatterometry tool 120, includes a light source 122 and a detector 124 positioned proximate the grating structure 300 and process layer 310. The light source 122 of the scatterometry tool 120 illuminates at least a portion of the process layer 310 and the grating structure 300, and the detector 124 takes optical measurements, such as intensity or phase, of the reflected light. A data processing unit 125 receives the optical measurements from the detector 124 and processes the data to determine an electromagnetic property (e.g., refractive index) of the process layer 310.

The scatterometry tool 120 may use monochromatic light, white light, or some other wavelength or combinations of wavelengths, depending on the specific implementation. The angle of incidence of the light may also vary, depending on the specific implementation. The light analyzed by the scatterometry tool 120 typically includes a reflected component (i.e., incident angle equals reflected angle) and a refracted component (i.e., incident angle does not equal the reflected angle). For purposes of discussion here, the term "reflected" light is meant to encompass both components.

Variations in the electromagnetic properties of the process layer 310 causes changes in the reflection profile (e.g., intensity vs. wavelength—tan($\delta$), phase vs. wavelength—cos($\psi$), where $\delta$ and $\psi$ are common scatterometry outputs known to those of ordinary skill in the art) measured by the scatterometry tool 120 as compared to the light scattering profile that would be present in a process layer 310 having an acceptable electromagnetic property.

Figure 4A:
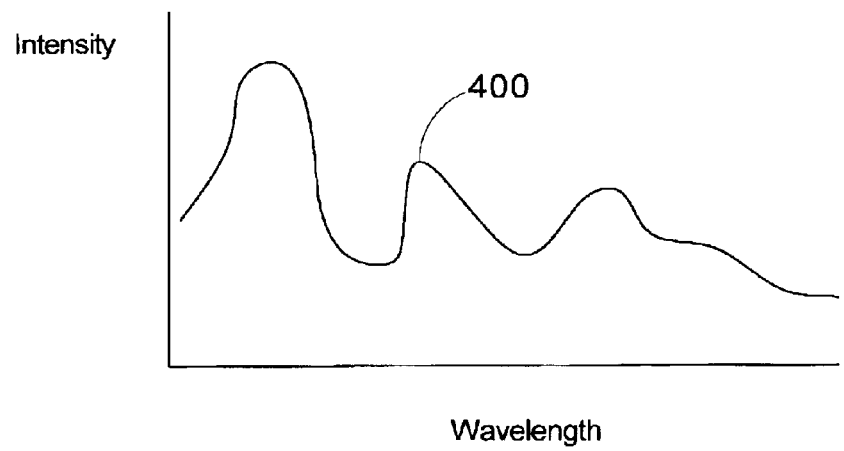
FIGS. 4A, 4B, and 4C illustrate a library of exemplary scatterometry curves used to characterize the wafer measured in the scatterometry tool of FIG. 3.
Figure 4B:
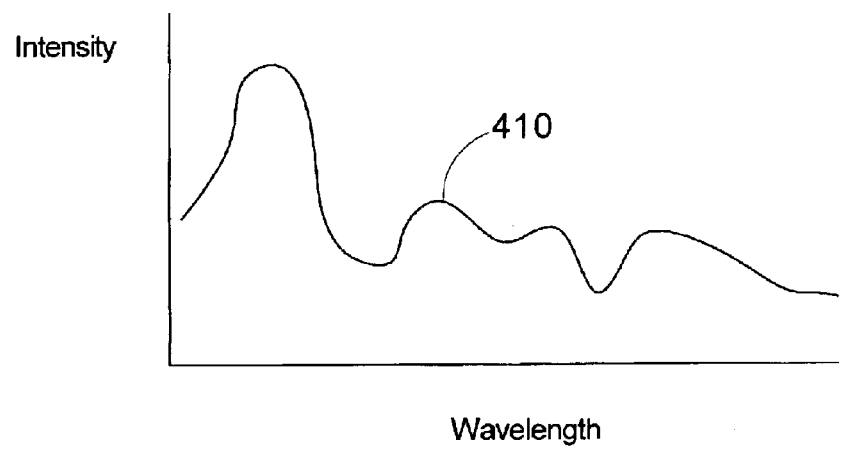
Figure 4C:
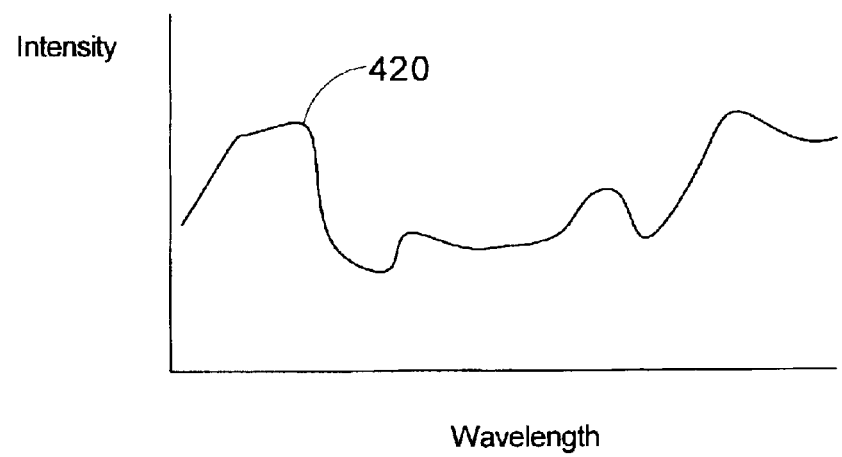

FIGS. 4A, 4B, and 4C illustrate exemplary reflection profiles 400, 410, 420 that may be included in a reference reflection profile library 128 (see FIG. 1) used by the data processing unit 125 to characterize the electromagnetic property of the process layer 310 based on the measured reflection profiles. As stated above, the thickness of the process layer 310 is determined prior to the scatterometry analysis. The reference reflection profile library 128 may represent reference profiles for a given thickness. Separate libraries or sub-libraries may be provided for differing thicknesses or ranges of thicknesses. The particular reflection profile expected for any structure depends on the specific geometry of the grating structure 300, the electromagnetic and electrical properties of the process layer 310, and the parameters of the measurement technique employed by the scatterometry tool 120 (e.g., light wavelength, angle of incidence, etc.). The profiles in the reference reflection profile library 128 are typically calculated theoretically by employing Maxwell's equations to model individual spectra based on the expected characteristics of the process layer 310 and the topology and geometry of the grating structure 300. Spectra are generated at a predetermined resolution for every profile that may be expected, and the sum of all said spectra constitute the reference reflection profile library 128. Scatterometry libraries are commercially available from Timbre Technologies, Inc. The profiles in the reference reflection profile library 128 may also be generated empirically by measuring reflection profiles of sample wafers and subsequently characterizing the measured wafers by destructive or non-destructive examination techniques. Alternatively, real time reflection profile analysis may be performed.

The reflection profile 400 of FIG. 4A represents an expected profile for a process layer 310 with a desired electromagnetic property for the process layer 310. The reflection profile 410 of FIG. 4B represents an expected profile for a process layer 310 that has a reduced electromagnetic property as compared to the desired electromagnetic property, and reflection profile 420 of FIG. 4C represents an expected profile for a process layer 310 that has an increased electromagnetic property as compared to the desired electromagnetic property. The reflection profiles of process layers 310 with varying electromagnetic property values may be included in the reference reflection profile library 128.

The data processing unit 125 compares the measured reflection profile to the reference reflection profile library 128. Each reference profile has an associated electromagnetic property metric. The data processing unit 125 determines the reference reflection profile having the closest match to the measured reflection profile. Techniques for matching the measured reflection profile to the closest reference reflection profile are well known to those of ordinary skill in the art, so they are not described in greater detail herein. For example, a minimum least squares or nearest neighbor approach may be used.

In another embodiment, the process controller 130 or other external controller (not shown) may be adapted to compare the measured reflection profile to the reference reflection profile library 128. In such a case, the scatterometry tool 120 would output the matching reference reflection profile, and the process controller 130 may link that reference reflection profile to an associated electromagnetic property metric.

In another embodiment, the measured reflection profile may be compared to a target reflection profile selected from the reference reflection profile library 128 for a process layer 310 having a known and desired electromagnetic property (e.g., the profile 400 of FIG. 4A). Different target profiles may be provided for different thicknesses or ranges of thicknesses. For example, a target reflection profile may be calculated for a process layer 310 having an ideal or acceptable electromagnetic property using Maxwell's equations, and that target reflection profile may be stored in the reference reflection profile library 128. Thereafter, the measured reflection profile of a process layer 310 having an unknown electromagnetic property is compared to the target reflection profile. Based upon this comparison, a relatively rough approximation of the electromagnetic property may be determined. That is, by comparing the measured reflection profile to the target reflection profile, the electromagnetic property of the process layer 310 may be approximated, such that further matching of the measured reflection profile with additional reference reflection profiles from the reference reflection profile library 128 is unwarranted. Using this technique, an initial determination may be made as to the electromagnetic property of the process layer 310. Of course, this step may be performed in addition to the matching or correlating of a measured reflection profile to a reference reflection profile from the reference reflection profile library 128 as described above.

After receiving the electromagnetic property metric from the scatterometry tool 120, the process controller 130 may take a variety of autonomous actions. In one embodiment of the present invention, the process controller 130 is adapted to modify the operating recipe of the deposition tool 110 based on the electromagnetic property metric to control deposition operations on subsequent wafers processed by the deposition tool 110.

Various operating recipe parameters of the deposition tool 110 may be controlled to affect the electromagnetic property of the deposited process layer 310. For example, commonly known recipe parameters that affect refractive index are chemical stoichiometry/composition, thickness, homogeneity/heterogeneity of film, gas settings (e.g., flow, pressure, temperature, for deposition processes), plasma settings (e.g., RF power and gap distance for plasma enhanced chemical vapor deposition), etc.

The process controller 130 may also control the operation of the deposition tool 110 in real time to affect the deposition process during the actual forming of the process layer 310. The scatterometry tool 120 periodically generates a measured reflection profile and determines the electromagnetic property of the process layer 310. The thickness of the process layer 310 at the time the scatterometry tool 120 is employed to affect the library or target profile used by the scatterometry tool 120. Operating recipe parameters, such as reactant gas stoichiometry, temperature, pressure, SOG spin speed, gap distance, RF power, etc. may be varied in real time to affect the electromagnetic property of the process layer 310.

The frequency of the measurements taken by the scatterometry tool 120 may be varied as a matter of design choice. For example, during a typical deposition process, the scatterometry tool 120 may generate a reflection profile approximately every 1–3 seconds. Measurements may also be taken at different rates during the duration of the deposition process, i.e., more measurements may be taken as the process nears endpoint. The deposition process may or may not be stopped during the period when the scatterometry measurements are being taken.

The process controller 130 may use a control model (not shown) of the deposition tool 110 for changing its operating recipe. For example, the process controller 130 may use a control model relating the measured electromagnetic property to a particular operating recipe parameter in the deposition tool 110 to correct for deviations in the electromagnetic property. The control model may be developed empirically using commonly known linear or non-linear techniques. The control model may be a relatively simple equation based model (e.g., linear, exponential, weighted average, etc.) or a more complex model, such as a neural network model, principal component analysis (PCA) model, or a projection to latent structures (PLS) model. The specific implementation of the model may vary depending on the modeling technique selected.

An electromagnetic property model may be generated by the process controller 130, or alternatively, it may be generated by a different processing resource (not shown) and stored on the process controller 130 after being developed. The electromagnetic property model may be developed using the deposition tool 110 or using a different tool (not shown) having similar operating characteristics. For purposes of illustration, it is assumed that the electromagnetic property model is generated and updated by the process controller 130 or other processing resource based on the actual performance of the deposition tool 110 as measured by the scatterometry tool 120. The electromagnetic property model may be trained based on historical data collected from numerous processing runs of the deposition tool 110.

Figure 5:
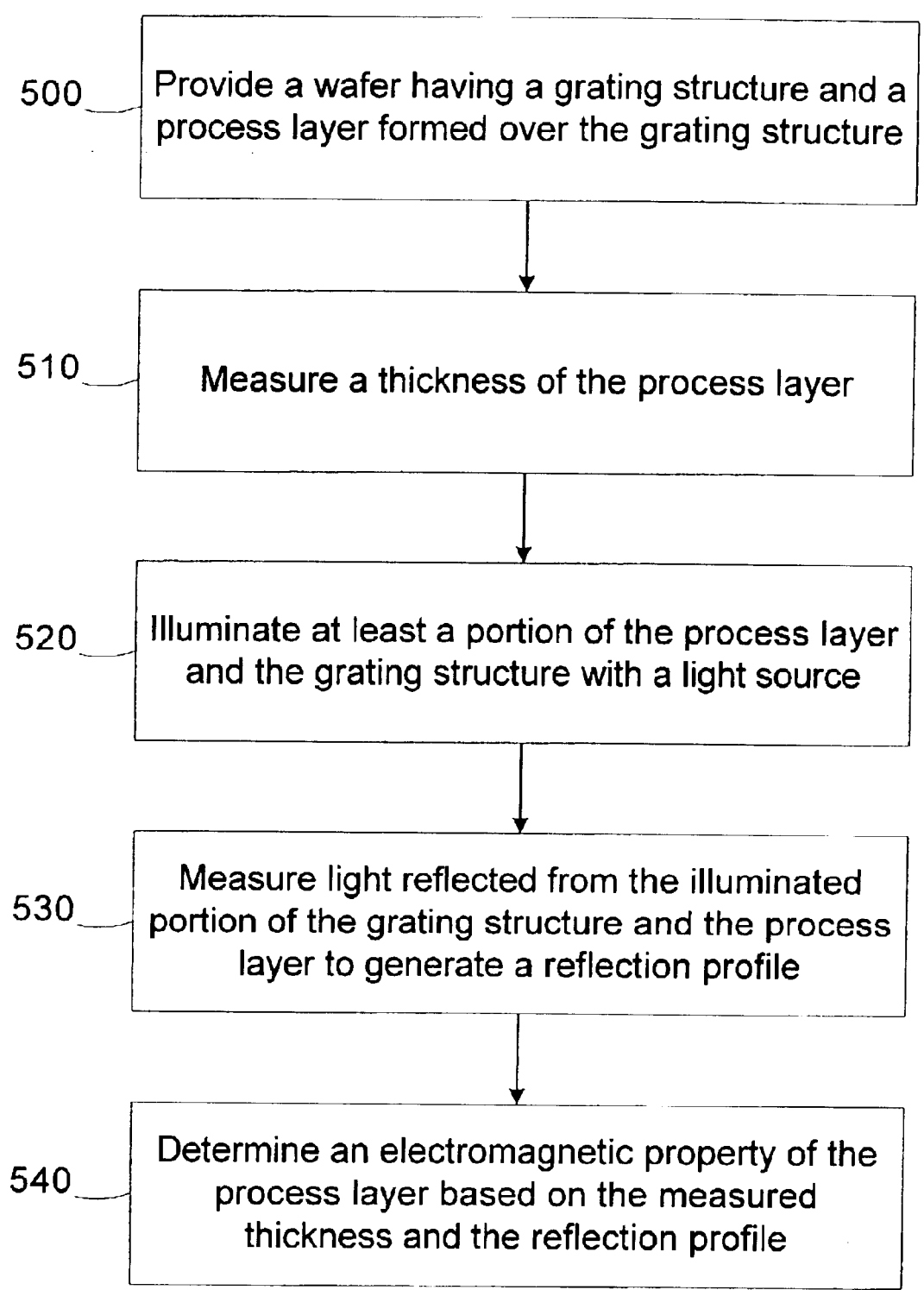
FIG. 5 is a simplified flow diagram of a method for determining electromagnetic properties of a process layer using scatterometry measurements in accordance with another illustrative embodiment of the present invention.

Referring now to FIG. 5, a simplified flow diagram of a method for determining properties of a process layer in accordance with another illustrative embodiment of the present invention is provided. In block 500, a wafer having a grating structure 300 and a process layer 310 formed over the grating structure 300 is provided. In block 510, a thickness of the process layer 310 is measured. In block 520, at least a portion of the process layer 310 and the grating structure 300 are illuminated with a light source. In block 530, light reflected from the illuminated portion of the grating structure 300 and process layer 310 is measured to generate a reflection profile. In block 540, an electromagnetic property of the process layer 310 is determined based on the measured thickness and the reflection profile.

Monitoring and controlling the electromagnetic properties of the process layer 310 based on feedback from the scatterometry tool 120, as described above, has numerous advantages. The deposition tool 110 may be controlled to decrease variability in the electromagnetic property of the process layer 310. Decreased variation increases the quality and performance of the devices produced on the processing line 100 and the efficiency of the processing line 100.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for determining electromagnetic properties of a process layer, comprising:

providing a wafer having a grating structure and a process layer formed over the grating structure;

measuring a thickness of the process layer;

illuminating at least a portion of the process layer and the grating structure with a light source;

measuring light reflected from the illuminated portion of the grating structure and the process layer to generate a reflection profile; and determining an electromagnetic property of the process layer based on the measured thickness and the reflection profile.

2. The method of claim 1, wherein determining the electromagnetic property of the process layer further comprises:
   comparing the generated reflection profile to a library of reference reflection profiles, each reference reflection profile having an associated electromagnetic property metric;
   selecting a reference reflection profile closest to the generated reflection profile; and
   determining the electromagnetic property of the process layer based on the electromagnetic property metric associated with the selected reference reflection profile.

3. The method of claim 2, further comprising selecting the entries in the library of reference reflection profiles based on the measured thickness.

4. The method of claim 1, wherein generating the reflection profile comprises generating the reflection profile based on at least one of intensity and phase of the reflected light.

5. The method of claim 1, wherein providing the wafer comprises providing the wafer having the grating structure formed in a test structure on the wafer.

6. The method of claim 1, wherein providing the wafer comprises providing the wafer having the grating structure formed in a production device on the wafer.

7. The method of claim 1, wherein determining the electromagnetic property of the process layer further comprises:
   comparing the generated reflection profile to a target reflection profile; and
   determining the electromagnetic property of the process layer based on the comparison of the generated reflection profile and the target reflection profile.

8. The method of claim 7, further comprising selecting the target reflection profile from a plurality of target reference profiles based on the measured thickness.

9. The method of claim 1, further comprising determining at least one parameter of an operating recipe of a deposition tool based on the determined electromagnetic property.

10. The method of claim 9, wherein determining the at least one parameter of the operating recipe further comprises determining at least one of a reactant gas stoichiometry parameter, a temperature parameter, a pressure parameter, a temperature parameter, and a plasma parameter.

11. The method of claim 1, wherein providing the wafer further comprises forming the process layer on the wafer, the process layer overlying the grating structure, and the method further comprises determining at least one parameter of an operating recipe of a deposition tool based on the determined electromagnetic property during the forming of the process layer.

12. The method of claim 11, wherein determining the at least one parameter of the operating recipe further comprises determining at least one of a reactant gas stoichiometry parameter, a temperature parameter, a pressure parameter, a temperature parameter, and a plasma parameter.

13. The method of claim 1, wherein determining the electromagnetic property of the process layer further comprises determining a refractive index of the process layer.

14. A method for determining electromagnetic properties of a process layer, comprising:
   providing a wafer having a grating structure and a process layer formed over the grating structure;
   measuring a thickness of the process layer;
   illuminating at least a portion of the process layer and the grating structure with a light source;
   measuring light reflected from the illuminated portion of the grating structure and the process layer to generate a reflection profile;
   comparing the generated reflection profile to a library of reference reflection profiles selected based on the measured thickness, each reference reflection profile having an associated electromagnetic property metric;
   selecting a reference reflection profile closest to the generated reflection profile; and
   determining an electromagnetic property of the process layer based on the electromagnetic property metric associated with the selected reference reflection profile.

15. The method of claim 14, wherein generating the reflection profile comprises generating the reflection profile based on at least one of intensity and phase of the reflected light.

16. The method of claim 14, wherein providing the wafer comprises providing the wafer having the grating structure formed in a test structure on the wafer.

17. The method of claim 14, wherein providing the wafer comprises providing the wafer having the grating structure formed in a production device on the wafer.

18. The method of claim 14, further comprising determining at least one parameter of an operating recipe of a deposition tool based on the determined electromagnetic property.

19. The method of claim 18, wherein determining the at least one parameter of the operating recipe further comprises determining at least one of a reactant gas stoichiometry parameter, a temperature parameter, a pressure parameter, a temperature parameter, and a plasma parameter.

20. The method of claim 14, wherein providing the wafer further comprises forming the process layer on the wafer, the process layer overlying the grating structure, and the method further comprises determining at least one parameter of an operating recipe of a deposition tool based on the determined electromagnetic property during the forming of the process layer.

21. The method of claim 20, wherein determining the at least one parameter of the operating recipe further comprises determining at least one of a reactant gas stoichiometry parameter, a temperature parameter, a pressure parameter, a temperature parameter, and a plasma parameter.

22. The method of claim 14, wherein determining the electromagnetic property of the process layer further comprises determining at least one of a refractive index, an extinction coefficient, and an index of refraction of the process layer.

23. The method of claim 14, further comprising selecting the entries in the library of reference reflection profiles based on the measured thickness.

24. A method for determining electromagnetic properties of a process layer, comprising:
   providing a wafer having a grating structure and a process layer formed over the grating structure;
   illuminating at least a portion of the process layer and the grating structure with a light source;
   measuring light reflected from the illuminated portion of the grating structure and the process layer to generate a reflection profile;
   selecting a target reflection profile based on the measured thickness;
   comparing the generated reflection profile to the selected target reflection profile; and determining an electromagnetic property of the process layer based on the comparison of the generated reflection profile and the target reflection profile.

25. The method of claim 24, wherein generating the reflection profile comprises generating the reflection profile based on at least one of intensity and phase of the reflected light.

26. The method of claim 24, wherein providing the wafer comprises providing the wafer having the grating structure formed in a test structure on the wafer.

27. The method of claim 24, wherein providing the wafer comprises providing the wafer having the grating structure formed in a production device on the wafer.

28. The method of claim 24, further comprising determining at least one parameter of an operating recipe of a deposition tool based on the determined electromagnetic property.

29. The method of claim 28, wherein determining the at least one parameter of the operating recipe further comprises determining at least one of a reactant gas stoichiometry parameter, a temperature parameter, a pressure parameter, a temperature parameter, and a plasma parameter.

30. The method of claim 24, wherein providing the wafer further comprises forming the process layer on the wafer, the process layer overlying the grating structure, and the method further comprises determining at least one parameter of an operating recipe of a deposition tool based on the determined electromagnetic property during the forming of the process layer.

31. The method of claim 30, wherein determining the at least one parameter of the operating recipe further comprises determining at least one of a reactant gas stoichiometry parameter, a temperature parameter, a pressure parameter, a temperature parameter, and a plasma parameter.

32. The method of claim 24, wherein determining the electromagnetic property of the process layer further comprises determining at least one of a refractive index, an extinction coefficient, and an index of refraction of the process layer.

33. A system method for determining electromagnetic properties of a process layer formed over a grating structure, comprising:

means for measuring a thickness of the process layer;

means for illuminating at least a portion of the process layer and the grating structure with a light source;

means for measuring light reflected from the illuminated portion of the grating structure and the process layer to generate a reflection profile; and means for determining an electromagnetic property of the process layer based on the measured thickness and the reflection profile.

* * * * *